United States Patent [19]

Raczkowski

[11] 4,033,337

[45] July 5, 1977

[54] SELF-DONNED SPHYGMOMANOMETER CUFF

[75] Inventor: Jan Raczkowski, Glendale, N.Y.

[73] Assignee: Propper Manufacturing Company, Inc., Long Island City, N.Y.

[22] Filed: Jan. 14, 1976

[21] Appl. No.: 648,867

[52] U.S. Cl. .......................... 128/2.05 C; 128/327; 128/DIG. 20
[51] Int. Cl.² ........................................ A61B 5/02
[58] Field of Search ................ 128/2.05 C, 2.05 G, 128/327, DIG. 20

[56] References Cited
UNITED STATES PATENTS

| | | |
|---|---|---|
| 3,120,846 | 2/1964 | Fletcher ...................... 128/2.05 C |
| 3,279,459 | 10/1966 | Schenker .................... 128/2.05 C |
| 3,606,880 | 9/1971 | Ogle ............................ 128/2.05 C |
| 3,669,096 | 6/1972 | Hurwitz ...................... 128/2.05 C |
| 3,906,937 | 9/1975 | Aronson ..................... 128/2.05 C |
| 3,968,788 | 7/1976 | Hopkins ...................... 128/2.05 C |

*Primary Examiner*—Kyle L. Howell

[57] ABSTRACT

A sphygmomanometer cuff which is adapted to be put on by a patient without assistance. One end of the cuff is formed into a loop by means of elastic bands extending around the loop. When the loop is slipped over a limb, the elastic bands stretch and hold the cuff in place while the remaining cuff portion is wrapped and secured.

8 Claims, 4 Drawing Figures

SELF-DONNED SPHYGMOMANOMETER CUFF

This invention relates generally to sphygmomanometer cuffs and more specifically to a cuff which is adapted to be used by patients without assistance.

It is frequently necessary for a patient to measure his own blood pressure. For example, it is common practice among doctors to treat hypertensive patients by prescribing drugs that, both as to dosage and composition, are customized to the particular individual. In arriving at the correct prescription for the individual, the doctor normally follows a testing program in which he prescribes a drug for the patient and monitors the effect of the drug on the patient's blood pressure. During such a testing program, it is frequently necessary for a patient to have his blood pressure taken several times a day. Such a testing program could go on for months before the eventual composition and dosage for the particular patient is arrived at. Under such circumstances, it is a great advantage to both the doctor and the patient if the patient can take his own blood pressure.

One of the difficulties encountered in a patient's taking his own blood pressure has been that the conventional sphygmomanometer cuff normally requires two free hands for application, and can be donned by the patient himself only with great difficulty. Prior art attempts have been made to provide convenient self-donned sphygmomanometer cuffs. For example, cuffs have been provided with one end folded back on the body to form a loop so that the cuff can be slipped over the limb and held in place for wrapping. This approach will accommodate only a small range of limb girths and, even if some portion of the loop is elastic, patients with thick limbs find it difficult or impossible to take their blood pressure because the elastic force exerted by the cuff restricts circulation.

It is therefore an object of this invention to enable patients to measure their own blood pressure in a convenient manner and to accommodate a wide range of limb girths.

It is another object of this invention to provide a sphygmomanometer cuff accomodating a wide range of limb girths which is conveniently self-donned.

It is another object of this invention to provide a sphygmomanometer cuff which can be self-donned and which will not interfere with blood circulation within the limb until pressure is measured.

In accordance with an illustrative embodiment demonstrating objects and features of the present invention, one end of a sphygmomanometer cuff body is formed into a loop which is retained by means of at least one elastic band closing the loop and extending around some part of its circumference. When a limb is inserted into the loop, the entire band stretches so that a broad range of limb girths can be accomodated with the cuff exerting a relatively low elastic force. Once the loop is on the limb and held in place by the elastic bands, the remainder of the cuff can be wrapped and rigidly secured by use of cooperating hook and pile material or other securing devices.

The foregoing and other objects, features and advantages of the present invention are best understood by reference to the following detailed description of a presently preferred embodiment of the invention when read in connection with the appended drawings in which.

Figure 1:
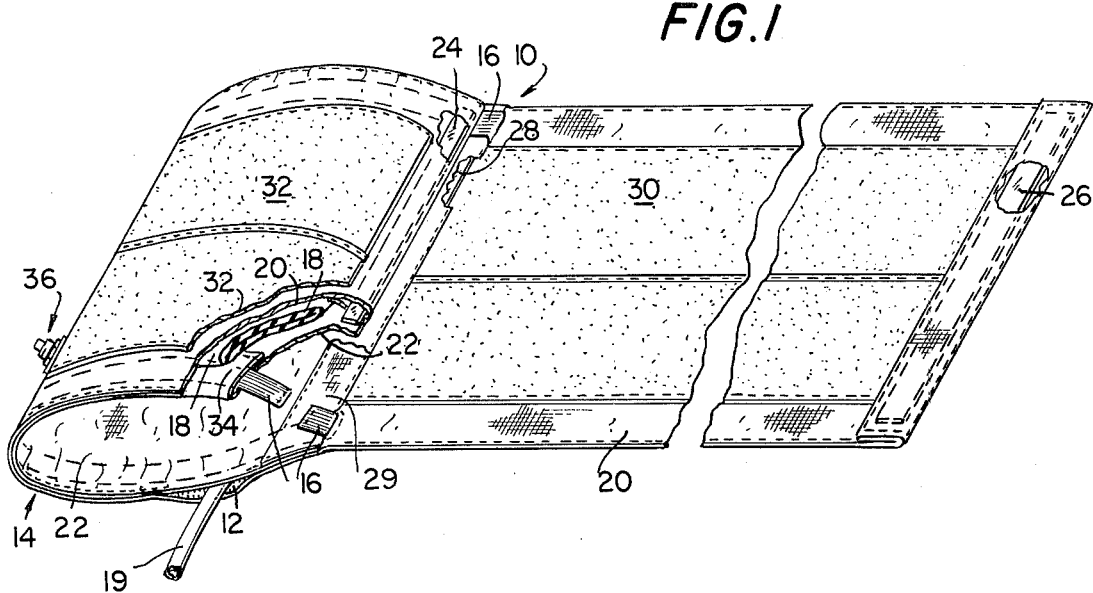
FIG. 1 is a perspective view with parts cut away of a sphygmomanometer cuff which incorporates the present invention.
Figure 2:
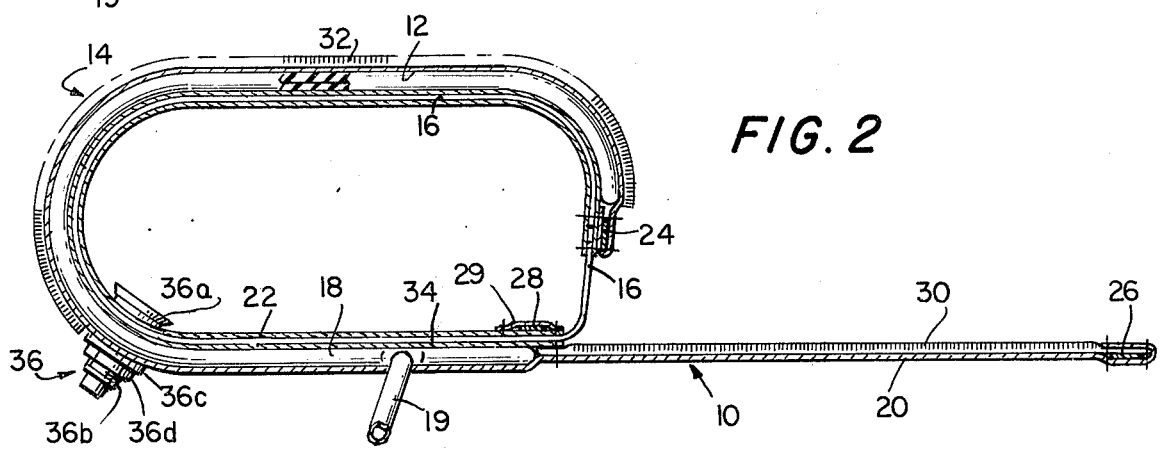
FIG. 2 is a front sectional view of the cuff of FIG. 1 showing the details of construction.

Referring now to the drawing and first to FIGS. 1 and 2, there is shown a sphygmomanometer cuff incorporating the invention. The main body of the cuff, indicated generally by 10, is made of flexible sheet material, for example, non-stretchable fabric and includes a section having an expandable pocket 12. The section of the cuff including pocket 12 is folded back on itself to form a loop portion indicated generally by 14, and is held in place by strips or bands of elastic material 16. These elastic bands internally encircle the circumference of loop portion 14 and are secured to the body in a manner to permit the entire bands to stretch when loop portion 14 is slipped over a limb. The cuff includes, within pocket 12, an inflatable bladder 18, which communicates with a conventional inflation device and manometer (not shown) via hose 19 and is effective to apply pressure to a limb when inflated.

The major component of cuff body 10 is strip 20 made of flexible sheet material, such as non-stretchable fabric. A second strip 22 of flexible sheet material is sewn along its edges in confronting relationship to strip 20 to form pocket 12. Preferably, strip 22 is made of slippery fabric to permit the cuff to be slid easily along the patients limb while it is being applied. Strip 22 is shorter than strip 20, so pocket portion 12 extends only part way between the ends of strip 20. Relatively rigid members 24 and 26 are sewn into hems at either end of strip 20 to stiffen the body of the cuff against widthwise flexing and a similar member 28 is sewn into a guideway 29 at the end of strip 22 disposed between the two ends of strip 20, for the same purpose. Guideway 29 is formed by sewing a narrow strip of fabric over and along the end of strip 22. Fastening surface 30, for example, a pile surface of the type manufactured under the trademark "VELCRO" by American Velcro Co., is sewn onto the top of the right-hand portion (in FIG. 1) of strip 20, which does not have pocket portion 12, and complimentary fastening surface 32, for example, a Velcro hook surface, is sewn on the under surface in the pocket portion of strip 20. Inasmuch as this under surface becomes the outside surface of the loop portion of the cuff, it can be seen that surfaces 30 and 32 will mate when the cuff is wrapped around a limb.

Elastic bands 16 close the loop 14 and extend around its circumference within hems 34 formed in the lengthwise edges of strip 22. These bands may be any form of conventional elastic material. In the illustrative embodiment, the elastic bands are sewn at a first end to the end of the cuff body including stiffening member 24, pass externally of the cuff body, reenter the cuff body at the interior end of strip 22 adjacent stiffening member 28 (thereby closing the loop), pass around the looped portion of the cuff within hem 34 and are again sewn to the end of the cuff body adjacent stiffening member 24. Any other arrangement for joining bands 16 to the cuff body will work equally well as long as the bands form a portion of the cuff body into a closed expandable loop 14 and a substantial length of bands 16, including the external portions and those guided in hems 34, is stretched when the loop 14 is placed over a patients limb. As a result, bands 16 can stretch to accomodate a wide range of limb girths without applying a sufficient force to the patients limb to impede circulation.

Bladder 18 is disposed within pocket portion 12 of the cuff body and is operative to expand the pocket portion. Bladder 18 can be any form of inflatable bladder conventionally used in sphymomanometer cuffs, with hose 19 being formed as a part of it. The seam between strips 20 and 22 in the vicinity of hose 14 is left unsewn to permit replacement of bladder 18 in the event that it should be punctured or otherwise damaged. Also, in the illustrative embodiment, the two side of the seam are provided with complimentary Velcro mating surfaces to realize a closed seam which may be opened when necessary.

A stethoscope head, indicated generally as 36, is mounted through a hole in pocket portion 12 of the cuff with its sensor 36a pointing into loop 14. Stethoscope head 36 may be any form of conventional stethoscope head and includes threaded shaft 36b useful to secure it in pocket portion 12 by means of washer 36c and nut 36d. This arrangement of the stethoscope head requires that shaft 36b extend through aligned holes in strips 20 and 22, and bladder 18. The hole in bladder 18 must, of course, be sealed.

Figure 3:
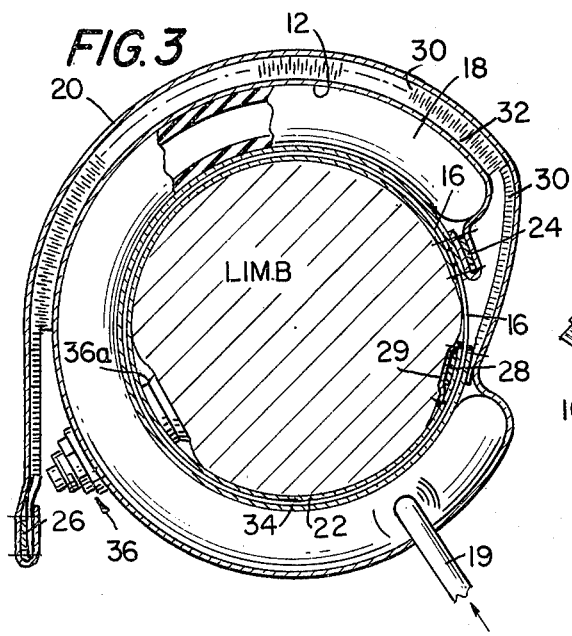
FIG. 3 is a sectional view of a cuff in accordance with the invention as it appears after being donned on a limb, wrapped and inflated.

In use, the loop portion 14 of the cuff is slipped over a limb, where it is held in place through the stretching force of elastic bands 16. The free portion of the cuff is then conveniently wrapped over the loop portion 14 to enclose the limb as indicated in FIG. 3. The cuff is held in this wrapped position through the engagement of complimentary fastening surfaces 30 and 32 which retain the cuff in an unyielding condition. The patient may listen to his pulse by connecting a conventional stethoscope ear piece (not shown) to the head 36. The blood pressure is taken in the conventional manner by listening for predetermined blood circulation sounds while deflating bladder 18.

Figure 4:
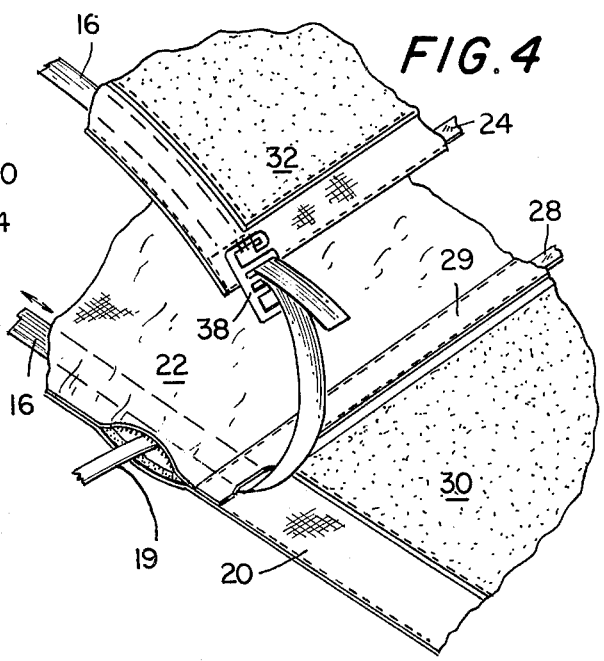
FIG. 4 is a perspective drawing indicating how the elastic bands may be modified to make them adjustable to accomodate exceptionally large or small girth limbs.

The perspective drawing of FIG. 4 illustrates how the cuff of FIG. 1 can be modified to make bands 16 adjustable so as to permit fitting an exceptionally broad range of limb girths. One end of bands 16 is sewn to the end of the cuff body including stiffening member 24. A pair of buckle type adjusters 38 are sewn to the same end of the cuff body. The external portion of each of bands 16 is then attached to one of the adjusters to preset the unstretched size of loop 14. Once this buckle adjustment is set, the excess elastic may be cut away. Otherwise, the modified cuff is identical to the illustrative embodiment already described.

Although specific embodiments of the invention have been described for illustrative purposes, it will be apparent to one skilled in the art that many mdoification, additions and substitutions are possible without departing from the scope and spirit of the disclosed invention. For example, bands 16 need not be guided within the body of the cuff, but could merely be held in contact with strip 22 on the inner surface of loop portion 14 by means of fabric loops or the like. Furthermore, bands 16 need not extend along loop portion 14, but could retain loop portion 14, as already described, and then extend along the free portion of the cuff or along the entire body of the cuff.

What is claimed is:

1. A sphymomanometer cuff adapted to be applied by a patient on his limb without assistance comprising a cuff body made of a flexible unstretchable sheet material terminating in first and second ends and having a pocket portion adapted to receive an inflatable bladder disposed between said first end and a point intermediate said ends; at least one elastic band having a portion passing between said intermediate point and said first end to form said body between said intermediate point and said first end into an expandable loop, and a portion extending along said body to a fastening point thereon; means for guiding said at least one band with respect to said body so that both portions of said at least one band are stretched when said expandable loop is applied over said limb; and means for removably securing the portion of said body lying between said intermediate point and said second end to said loop to form an unyielding loop.

2. The cuff of claim 1 in which said fastening point is disposed between said first end and said intermediate point.

3. The cuff of claim 2 in which said at least one band is secured at one end thereof to said body at one of said first end and said intermediate point and at the other end thereof to said fastening point said guiding means guiding said band between said fastening point and the other of said first end and said intermediate point.

4. The cuff of claim 1 in which said guiding means comprises at least one hem extending between said first end and said intermediate point.

5. The cuff of claim 1 in which said body further includes a plurality of relatively rigid stiffening members secured to said body so as to be transverse to a line drawn between said first and second ends, said members being distributed along said body between said ends with one member at each of said first and second ends and one member at said intermediate point.

6. A cuff accordig to claim 1 in which said body has a slit in said pocket portion permitting insertion and removal of said inflatable bladder and further includes means for openably closing said slit.

7. A cuff according to claim 1 further comprising a stethoscope head secured to said body to contact said limb when said cuff is donned.

8. The cuff of claim 1 further comprising means for adjusting the length of said at least one band.

* * * * *